United States Patent [19]
Abma et al.

[11] Patent Number: 5,654,463
[45] Date of Patent: Aug. 5, 1997

[54] ORGANIC PEROXIDE STABILIZATION WITH α-HYDROXYALKYL PEROXIDES

[75] Inventors: Charles Abma, Marshall; Peter Frenkel, Longview, both of Tex.

[73] Assignee: Witco Corporation, Greenwich, Conn.

[21] Appl. No.: 656,072

[22] Filed: May 31, 1996

[51] Int. Cl.$^6$ .................................................. C07C 409/32
[52] U.S. Cl. ............................................ 558/261; 558/264
[58] Field of Search ...................................... 558/261, 264

[56] References Cited

U.S. PATENT DOCUMENTS

| | | | |
|---|---|---|---|
| 2,415,971 | 2/1947 | Stevens | 558/261 X |
| 2,491,397 | 12/1949 | Stevens | 558/261 |
| 3,775,341 | 11/1973 | Barter | 558/261 X |
| 3,956,396 | 5/1976 | Mageli et al. | 568/559 |

*Primary Examiner*—Johann Richter
*Assistant Examiner*—Michael G. Ambrose
*Attorney, Agent, or Firm*—Scully, Scott, Murphy & Presser

[57] ABSTRACT

Organic peroxide compositions which contain an α-hydroxyalkyl peroxide compound to retard the rate of decomposition of the peroxide compound are disclosed.

14 Claims, No Drawings

ORGANIC PEROXIDE STABILIZATION WITH α-HYDROXYALKYL PEROXIDES

BACKGROUND OF THE INVENTION

The present invention relates to organic peroxide compositions, and more specifically to peroxydicarbonate compositions, in which an α-hydroxyalkyl peroxide has been added to retard the rate of decomposition of the peroxide compound.

Organic peroxides, such as peroxydicarbonates, are useful as free-radical initiators in the polymerization or copolymerization of ethylenically unsaturated monomers.

For example, organic peroxides are used as initiators in the polymerization of vinyl halides, such as vinyl chloride or vinyl bromide; vinylidene halides such as vinylidene chloride; and other compounds containing polymerizable unsaturated units. The products of this well known polymerization process have extensive commercial applications.

The polymerization of vinyl halides or the copolymerization of vinyl halides with vinylidene halides is usually conducted in an aqueous medium, i.e., emulsion, solution or suspension polymerization. In such polymerizations, the monomer or mixture of monomers is dispersed in water in the presence of a surfactant and thereafter the polymerization initiated with an organic peroxide. This is a well known reaction that has been widely reported.

All organic peroxides are by their nature hazardous materials. Their usefulness depends on their ability to decompose into free radicals, shown by the following reaction:

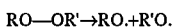

$$RO-OR' \rightarrow RO\cdot + R'O\cdot$$

The rate of this decomposition reaction at any given temperature depends on the structure of R and R'.

The decomposition reaction is exothermic. If exothermic decomposition were to occur during production, storage, or shipment, when the peroxides are in a concentrated form, excess pressure development and/or fire or explosion could result. Consequently, many organic peroxides must be kept refrigerated.

There have been several reports in recent years of the retardation of the rate of decomposition of organic peroxides.

The Journal of the American Chemical Society, Volume 72, pages 1254 to 1263 (1950) discloses the use of, for example, ethyl acetoacetate, iodine, trinitrobenzene, acetanilide, nitromethane, phenol, hydrogen peroxide and tetralin to retard the rate of decomposition of diisopropyl peroxydicarbonate.

U.S. Pat. No. 4,515,929 (1985) reports aqueous dispersions of organic peroxides including peroxydicarbonates, which are stabilized against decomposition by the addition of diphenyl peroxydicarbonate or di(alkyl substituted) phenyl peroxydicarbonates.

U.S. Pat. No. 4,552,682 (1985) discloses the use of phenolic antioxidants to retard the rate of degradation of aqueous dispersions of organic peroxides. The use of phenolic antioxidants is undesirable because they result in discoloration.

U.S. Pat. No. 5,155,192 (1992) discloses the use of organic hydroperoxides, e.g., tert-butyl hydroperoxide, to retard the rate of decomposition of peroxydicarbonates.

Research Disclosure, April, 1995, page 275, reports the thermal stabilization of dialkyl peroxydicarbonates using unsaturated nitriles or unsaturated acetylenic compounds.

SUMMARY OF THE INVENTION

The present invention relates to the use of certain compounds which are effective in retarding the rate of decomposition of organic peroxides, such as peroxydicarbonates. Thus, one aspect of the present invention is a composition containing an organic peroxide compound, such as a peroxydicarbonate, and an α-hydroxyalkyl peroxide which reduces the rate of decomposition of the peroxide. Another aspect of the present invention is the method of stabilizing a peroxydicarbonate against decomposition, comprising adding thereto an α-hydroxyalkyl peroxide in an amount effective to achieve said stabilization.

In particular, α-hydroxyalkyl peroxide compounds useful in the present invention include those of formulas I and II

wherein $R^1$ is hydrogen, hydroxy, alkyl containing 1 to 22 carbon atoms, phenyl, or phenyl substituted with one or more of alkyl containing 1–22 carbon atoms, halogen, and hydroxy;

$R^2$ and $R^3$ are each independently hydrogen, alkyl containing 1 to 22 carbon atoms, phenyl, or phenyl substituted with one or more of alkyl containing 1–22 carbon atoms, halogen, and hydroxy; or together $R^2$ and $R^3$ and the carbon atom to which they are attached may form a cycloalkyl ring containing from 4 to 10 carbon atoms;

$R^4$ and $R^5$ are each independently hydrogen, alkyl containing 1 to 22 carbon atoms, phenyl, or phenyl substituted with one or more of alkyl containing 1–22 carbon atoms, halogen, and hydroxy; or together $R^4$ and $R^5$ and the carbon atom to which they are attached may form a cycloalkyl ring containing from 4 to 10 carbon atoms;

in formula II, n is 1–10;

$R^6$ is hydrogen, alkyl containing 1 to 22 carbon atoms, hydroxy, phenyl, or phenyl substituted with one or more of alkyl containing 1–22 carbon atoms, halogen, and hydroxy;

$R^7$ and $R^8$ are each independently hydrogen, alkyl containing 1 to 22 carbon atoms, phenyl, or phenyl substituted with one or more of alkyl containing 1–22 carbon atoms, halogen, and hydroxy;

$R^9$ and $R^{10}$ are each independently hydrogen, alkyl containing 1 to 22 carbon atoms, phenyl, or phenyl substituted with one or more of alkyl containing 1–22 carbon atoms, halogen, and hydroxy.

DETAILED DESCRIPTION OF THE INVENTION

The present invention relates to compositions containing a peroxydicarbonate and an α-hydroxyalkyl peroxide to retard the rate of the decomposition of the peroxydicarbonate compound.

α-Hydroxyalkyl peroxides useful in the present invention may be of one of the following general formulas:

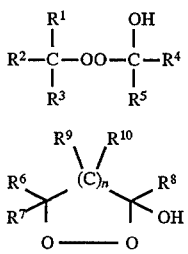

$$\begin{array}{c} R^1 \quad OH \\ | \quad\quad | \\ R^2-C-OO-C-R^4 \\ | \quad\quad | \\ R^3 \quad R^5 \end{array} \quad (I)$$

$$\begin{array}{c} R^9 \quad R^{10} \\ \backslash / \\ R^6 \diagdown (C)_n \diagup R^8 \\ R^7 \diagup \quad | \quad \diagdown OH \\ O \longrightarrow O \end{array} \quad (II)$$

In formula I defined above, $R^1$ is hydrogen, alkyl containing 1–22 carbon atoms, phenyl, substituted phenyl, or hydroxy. The phrase "substituted phenyl" refers to phenyl substituted with alkyl containing 1 to 22 carbon atoms, halogen (i.e. fluorine, chlorine, bromine, and/or iodine), and/or hydroxy, or with any two or more of any such groups. That is, when two or more of such substituents are present they can be the same or different.

$R^2$ and $R^3$ are each independently hydrogen, alkyl containing 1–22 carbon atoms, phenyl, substituted phenyl, or together $R^2$ and $R^3$ and the carbon atom to which they are attached may form a cycloalkyl ring of from 4 to 10 carbon atoms;

$R^4$ and $R^5$ are each independently hydrogen, alkyl containing 1–22 carbon atoms, phenyl, substituted phenyl, or together $R^4$ and $R^5$ and the carbon atom to which they are attached may form a cycloalkyl ring of from 4 to 10 carbon atoms.

In formula II above, n is 1–10, and preferably 1;

$R^6$ is hydrogen, alkyl containing 1–22 carbon atoms, phenyl, substituted phenyl, or hydroxyl;

$R^7$ and $R^8$ are each independently hydrogen, alkyl containing 1–22 carbon atoms, phenyl, or substituted phenyl;

$R^9$ and $R^{10}$ are each independently hydrogen, alkyl containing 1–22 carbon atoms, phenyl, or substituted phenyl.

In all cases, alkyl substituents can be straight-chain; or branched; cycloalkyl or cycloalkyl-alkyl. The cycloalkyl structure in the latter two cases may optionally be alkyl substituted.

Preferred embodiments useful in the present invention include compounds of Formula I such as hydroxymethyl-t-butyl peroxide (wherein $R^1$, $R^2$, and $R^3$ are each methyl, $R^4$ and $R^5$ are each hydrogen); hydroxymethyl-t-amyl peroxide (wherein $R^1$ and $R^2$ are each methyl, $R^3$ is ethyl, and $R^4$ and $R^5$ are each hydrogen); 1,1'-dihydroxy dicyclohexyl peroxide (wherein $R^1$ is hydroxy, $R^2$ and $R^3$ together with the carbon atom to which they are attached form a cyclohexyl ring, and $R^4$ and $R^5$ together with the carbon atom to which they are attached form a cyclohexyl ring); and 1,1'-dihydroxy dibenzyl peroxide (wherein $R^1$ is hydroxy, $R^2$ and $R^4$ are each phenyl, and $R^3$ and $R^5$ are each hydrogen).

Other preferred embodiments useful in the present invention include compounds of formula II, such as 3,5-dimethyl-3,5-dihydroxy-1,2-dioxacyclopentane (wherein n is 1, $R^6$ is hydroxy, $R^7$ and $R^8$ are each methyl, and $R^9$ and $R^{10}$ are each hydrogen).

Compounds of formula I wherein $R^1$, $R^2$ and $R^3$ are alkyl, and $R^4$ and $R^5$ are hydrogen, can be made by reacting equimolar amounts of formalin (37 wt.% formaldehyde in water) with a tertiary hydroperoxide, at 8° C. for 30 minutes and then vacuum distilling the product. Information concerning the synthesis of these compounds is found in U.S. Pat. No. 2,400,041, the disclosure of which is hereby incorporated by reference herein.

Compounds of formula I wherein $R^2$ and $R^3$ form a cycloalkyl ring can be made by reacting the corresponding cyclic ketone with 30% hydrogen peroxide which had been neutralized with sodium carbonate (mole ratio hydrogen peroxide: ketone=1:2), followed by filtration, washing and drying. Details can be found in the Journal of Applied Chemistry, USSR, volume 40, pages 2443–2448 (1967).

Compounds of formula I wherein $R^1$ is hydroxy, and $R^2$ and $R^4$ are each hydrogen, and $R^3$ and $R^5$ are each alkyl, can be made by reacting an aldehyde with dilute hydrogen peroxide (mole ratio of hydrogen peroxide: aldehyde=1:2), followed by filtration of the product, washing and drying. These types of compounds are discussed in D. Swern, ed., Organic Peroxides, Volume I, pages 25–26 (John Wiley and Sons, Inc., 1970).

Compounds of formula II can be prepared according to the procedure published in the Journal of the American Chemical Society, volume 85, pages 222–225 (1963).

The amount of α-hydroxyalkyl peroxide stabilizer to use in the compositions of the present invention is an amount sufficient to retard the rate of decomposition of the peroxydicarbonate. The preferred amount of stabilizer is 0.1–5.0% by weight of the peroxydicarbonate present, and most preferably 0.5–3.0% by weight thereof. The exact amount will vary and depend on both the peroxydicarbonate and the α-hydroxyalkyl peroxide used, and on the conditions to which the composition is to be exposed.

Peroxydicarbonate compounds useful in this invention are of the general structural formula (III):

$$R^{11}-(O)-C(O)-O-O-C(O)-(O)-R^{12} \quad (III)$$

wherein $R^{11}$ and $R^{12}$ can each be an aliphatic, cycloaliphatic or aromatic group with 1 to 22 carbon atoms, preferably 2 to 8 carbon atoms. $R^{11}$ and $R^{12}$ may be branched or non-branched, substituted or unsubstituted alkyl, alkenyl, cycloalkyl or aromatic groups.

Examples of $R^{11}$ and $R^{12}$ groups include phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxyphenyl, 2-ethoxyethyl, 2-ethoxyphenyl, 3-methoxybutyl, 2-carbamyloxyethyl, 2-chloroethyl, 2-nitrobutyl and 2-nitro-2-methylpropyl.

Specific examples of peroxydicarbonates include diethyl peroxydicarbonate, di-n-butyl peroxydicarbonate, diisobutyl peroxydicarbonate, and di-4-tert-butylcyclohexyl peroxydicarbonate. Preferably the peroxydicarbonate is di-sec-butyl peroxydicarbonate, di-2-ethylhexyl peroxydicarbonate, di-n-propyl peroxydicarbonate or diisopropyl peroxydicarbonate.

The peroxide compound may be symmetrical or unsymmetrical, i.e., $R^{11}$ and $R^{12}$ may be the same or different. The peroxide may be a homogeneous mixture containing symmetric peroxides, asymmetric peroxides such as isopropyl-sec-butyl peroxydicarbonate, or a mixture of symmetric and asymmetric peroxides such as mixtures of diisopropyl peroxydicarbonate, di-sec-butyl peroxydicarbonate and isopropyl-sec-butyl peroxydicarbonate as disclosed in U.S. Pat. No. 4,269,726.

The peroxydicarbonate compounds can be synthesized by conventional techniques familiar to one of ordinary skill in the art. Peroxydicarbonates are typically prepared by reacting the corresponding alkyl chloroformate with aqueous sodium peroxide at low temperatures, 0°–20° C. See U.S. Pat. No. 2,370,588 and the Journal of the American Chemical Society, Volume 72, page 1254 (1950). Other synthetic techniques will be familiar to one of ordinary skill in the art.

Preferably, the peroxydicarbonates useful in this invention include those which are a liquid at 0° C. and more preferably a liquid at −5° C. Still more preferred are the peroxydicarbonates which are liquid down to −20° C.

The present invention is especially applicable to aqueous dispersions of peroxydicarbonates that are useful as initiators in the free radical polymerization of ethylenically unsaturated materials, particularly in an aqueous medium, e.g., suspension or emulsion polymerization. A dispersion of the peroxydicarbonate is prepared by dispersing it in water with a suitable dispersing aid, e.g., a surfactant or emulsifying agent. Surfactants and emulsifying agents useful in the formulation of such dispersions are well known in this field and are quite numerous.

To prepare dispersions in accordance with the present invention, the α-hydroxyalkyl peroxide compound may be added to an already-formed peroxide dispersion, or to the water containing the surfactant, or to the peroxide before the dispersion is formed. Dispersions of the present invention generally contain 20 to 70% by weight, preferably 30 to 60% by weight, of the peroxydicarbonate compound and 0.5 to 3.0% (by weight of the peroxydicarbonate) of α-hydroxyalkyl peroxide.

The manner of preparation of peroxide dispersions is known to one of ordinary skill in the art. A description of peroxydicarbonate dispersions and their preparation can be found in U.S. Pat. No. 4,515,929; U.S. Pat. No. 3,825,509; U.S. Pat. No. 3,988,261 and U.S. Pat. No. 4,092,470.

Peroxydicarbonate compositions of the present invention may also be prepared as physical mixtures in the form of liquids, granules, powders or flakes. A physical mixture in accordance with the present invention may be prepared by mixing a liquid peroxide compound, or a solution of a peroxide in a suitable solvent, with the desired amount of α-hydroxyalkyl peroxide in a conventional mixing apparatus. The resulting mixture is then, if desired, granulated, pulverized or flaked. The α-hydroxyalkyl peroxide may be added either (1) to the chloroformate-containing reaction mixture before preparation of the peroxide compound or (2) to the unprocessed reaction mixture immediately after the preparation of the peroxide compound. Either (1) or (2) will ensure that the two components are mixed as homogeneously as possible in order to receive the greatest possible benefit from the stabilizing effect of the α-hydroxyalkyl peroxide.

A solution of the present invention may be prepared by combining the desired amounts of α-hydroxyalkyl peroxide compound and peroxydicarbonate in a suitable solvent.

Suitable organic solvents include those normally employed for peroxydicarbonates such as esters of phthalic acid, an example of which is dibutyl phthalate, and aliphatic and aromatic hydrocarbons and mixtures of such hydrocarbons, examples of which are hexane, odorless mineral spirits, mineral oil, benzene, toluene, xylene and (iso) paraffins such as isododecane. Other suitable solvents will be familiar to one of ordinary skill in the art.

Solutions according to the present invention preferably contain at least 10% by weight and more preferably at least 25% by weight of a peroxydicarbonate compound.

The peroxide compositions of the present invention display numerous significant advantages. Chief among these is improved thermal stability, both in response to exposure to elevating temperature and in response to a given constant temperature. Thermal stability of self-reactive substances in response to elevating temperatures can be determined by measuring the self accelerating decomposition temperature (SADT). SADT is one of the recognized characteristics for determining the safe storage and transportation of materials such as organic peroxides. [Recommendations on the Transport of Dangerous Goods, 9th ed, United Nations, NY 1995, Section 11.3.5, page 264].

SADT can be directly correlated with the onset temperature as measured in a differential thermal analyzer (DTA). The onset temperature is the point at which an uncontrolled thermal decomposition starts. The onset temperature can be measured by determining the point at which the rate of temperature increase in a sealed cell exceeds a certain predetermined value. In addition, the onset temperature can be measured by determining the point at which the rate of pressure increase in the sealed cell exceeds a certain predetermined value.

Thermal stability in response to a given constant temperature can be assessed by means of accelerated aging tests at, for instance, 15° C.

The α-hydroxyalkyl peroxides of the present invention increase the onset temperature of peroxydicarbonates. Also, the α-hydroxyalkyl peroxides do not detract from the effectiveness of the peroxydicarbonate as a polymerization initiator.

The following examples are intended to illustrate the claimed invention and are not in any way designed to limit its scope. Numerous additional embodiments within the scope and spirit of the claimed invention will become apparent to those skilled in the art.

EXAMPLE 1

The onset temperature was measured for samples of pure di-2-ethylhexyl peroxydicarbonate, di-2-ethylhexyl peroxydicarbonate diluted in odorless mineral spirits (OMS), and di-sec-butyl peroxydicarbonate diluted in OMS. The onset temperature was also measured for samples of the aforementioned peroxydicarbonates in the presence of various amounts of α-hydroxyalkyl peroxides. The liquid mixtures were prepared by dissolving the required amount of the α-hydroxyalkyl peroxide in the peroxydicarbonate.

Using a type of Differential Thermal Analyzer (Radex Solo Thermal Analyzer, marketed by Astra Scientific International, Pleasanton, Calif.), with an isothermal hold temperature of 30° C. for 15 minutes and then a temperature increase of 1°/minute to 130° C., the onset temperature was measured for a one gram sample of the peroxydicarbonate in a sealed cell. The onset temperature was measured both by noting the point where the rate of increase ($\Delta T$) of the sample temperature reached 0.2° C./minute and also the point where the rate of increase in pressure ($\Delta P$) of the closed sample cell reached 1.0 psi/minute. $\Delta T$ is the difference between the oven temperature and the sample temperature. $\Delta P$ is the difference between a reference pre-calibrated pressure and the pressure developed in the sealed sample cell.

The results, presented in Table I, show that the presence of α-hydroxyalkyl peroxides increases the temperature at which self accelerating decomposition of the peroxydicarbonate will begin. This shows that α-hydroxyalkyl peroxides are effective stabilizers of peroxydicarbonates.

TABLE I

Onset Temperature For Peroxydicarbonates Stabilized With α-Hydroxyalkyl Peroxides

| Peroxydicarbonate | Wt. % of Pure Additive Used | Onset Temp (C°.) by ΔT | Onset Temp (C°.) by ΔP |
|---|---|---|---|
| 97.7% Di-2-ethylhexyl Peroxydicarbonate (pure) | none | 36.3 | 42.3 |
| 97.7% Di-2-ethylhexyl Peroxydicarbonate (pure) | 3.0% HMBP | 44.3 | 47.3 |
| 97.7% Di-2-ethylhexyl Peroxydicarbonate (pure) | 3.0% HMAP | 46.4 | 49.2 |
| 97.7% Di-2-ethylhexyl Peroxydicarbonate (pure) | 1.0% HMAP | 41.3 | 43.6 |
| 97.7% Di-2-ethylhexyl Peroxydicarbonate (pure) | 1.0% DHDCHP in IPA* | 48.0 | 50.1 |
| 98.3% Di-2-ethylhexyl Peroxydicarbonate (pure) | none | 36.3 | 42.3 |
| 98.3% Di-2-ethylhexyl Peroxydicarbonate (pure) | 3.1% DHDBP in EG** | 41.6 | 44.9 |
| 74.8% Di-2-ethylhexyl Peroxydicarbonate in OMS | none | 41.4 | 43.6 |
| 74.8% Di-2-ethylhexyl Peroxydicarbonate in OMS | 1.0% HMBP | 42.7 | 46.4 |
| 74.8% Di-2-ethylhexyl Peroxydicarbonate in OMS | 2.0% HMBP | 45.0 | 48.2 |
| 74.8% Di-2-ethylhexyl Peroxydicarbonate in OMS | 3.0% HMBP | 46.8 | 48.6 |
| 74.8% Di-2-ethylhexyl Peroxydicarbonate in OMS | 3.8% HMBP | 47.2 | 49.4 |
| 74.8% Di-2-ethylhexyl Peroxydicarbonate in OMS | 4.7% HMBP | 47.1 | 49.6 |
| 74.8% Di-2-ethylhexyl Peroxydicarbonate in OMS | 1.0% HMAP | 45.7 | 47.5 |
| 74.8% Di-2-ethylhexyl Peroxydicarbonate in OMS | 2.9% HMAP | 48.6 | 50.1 |
| 74.8% Di-2-ethylhexyl Peroxydicarbonate in OMS | 0.2% DHDCHP in IPA*** | 44.3 | 46.5 |
| 74.8% Di-2-ethylhexyl Peroxydicarbonate in OMS | 0.4% DHDCHP in IPA*** | 48.6 | 50.3 |
| 74.8% Di-2-ethylhexyl Peroxydicarbonate in OMS | 1.1% DHDCHP in IPA*** | 49.1 | 50.7 |
| 74.8% Di-2-ethylhexyl Peroxydicarbonate in OMS | 1.4% DHDCHP in DMM* | 49.7 | 48.8 |
| 74.8% Di-2-ethylhexyl Peroxydicarbonate in OMS | 1.6% DHDCHP in EG* | 50.6 | 51.0 |
| 74.8% Di-2-ethylhexyl Peroxydicarbonate in OMS | 1.9% DMDHCP | 42.7 | 44.3 |
| 76.2% Di-sec-butyl Peroxydicarbonate in OMS | none | 36.6 | 41.0 |
| 76.2% Di-sec-butyl Peroxydicarbonate in OMS | 2.9% HMBP | 40.3 | 42.5 |
| 76.2% Di-sec-butyl Peroxydicarbonate in OMS | 2.9% HMAP | 40.1 | 44.8 |
| 76.2% Di-sec-butyl Peroxydicarbonate in OMS | 1.0% DHDCHP in IPA* | 41.4 | 43.9 |

HMBP = hydroxymethyl-t-butyl peroxide
HMAP = hydroxymethyl-t-amyl peroxide
DHDCHP = 1,1'-dihydroxy-dicyclohexyl peroxide
DHDBP = 1,1'-dihydroxy-dibenzyl peroxide
DMDHCP = 3,5-dimethyl-3,5-dihydroxy-1,2-dioxacyclopentane
IPA = isopropyl alcohol
DMM = dimethyl malonate
EG = ethylene glycol
*added as 50% solution
**added as 30% solution
***added as 20% solution

EXAMPLE 2

The effect of the presence of α-hydroxyalkyl peroxides on the storage stability at 15° C. of pure di-2-ethylhexyl peroxydicarbonate, di-2-ethylhexyl peroxydicabonate diluted in odorless mineral spirits (OMS), and di-sec-butyl peroxydicarbonate diluted in OMS, was determined as an accelerated aging test. The purity of the peroxydicarbonate was measured at weekly intervals. The results, presented in Tables II and III, show that α-hydroxyalkyl peroxides are effective stabilizers of peroxydicarbonates.

TABLE II

Purity vs. Time at 15° C. for Peroxydicarbonates Stablilized with α-Hydroxyalkyl Peroxides
(DHDCHP was added as 50% solution in the indicated solvent)

| Peroxydicarbonate | Wt. % Pure Additive Used | % Purity After Storage 1 week | % Purity After Storage 2 weeks |
|---|---|---|---|
| 98.2% Di-2-ethylhexyl Peroxydicarbonate (pure) | None | 32.1 | 17.5 |
| 98.2% Di-2-ethylhexyl Peroxydicarbonate (pure) | 0.2% DHDCHP in EG | 43.2 | 20.5 |
| 98.2% Di-2-ethylhexyl Peroxydicarbonate (pure) | 0.3% DHDCHP in EG | 42.8 | 20.6 |
| 98.2% Di-2-ethylhexyl Peroxydicarbonate (pure) | 0.5% DHDCHP in EG | 50.9 | 23.9 |
| 98.2% Di-2-ethylhexyl Peroxydicarbonate (pure) | 1% DHDCHP in EG | 71.9 | 31.1 |
| 98.2% Di-2-ethylhexyl Peroxydicarbonate (pure) | 1% DHDCHP in IPA | 55.9 | 23.5 |
| 98.2% Di-2-ethylhexyl Peroxydicarbonate (pure) | 1% DHDCHP in DMM | 51.8 | 26.4 |
| 73.0% Di-2-ethylhexyl Peroxydicarbonate in OMS | none | 30.6 | 17.6 |
| 73.0% Di-2-ethylhexyl Peroxydicarbonate in OMS | 0.5% DHDCHP in EG | 45.8 | 18.3 |
| 73.0% Di-2-ethylhexyl Peroxydicarbonate in OMS | 1.0% DHDCHP in EG | 59.9 | 29.6 |
| 73.0% Di-2-ethylhexyl Peroxydicarbonate in OMS | 1.6% DHDCHP in EG | 58.3 | 43.2 |
| 73.0% Di-2-ethylhexyl Peroxydicarbonate in OMS | 0.5% DHDCHP in IPA | 54.9 | 22.2 |
| 73.0% Di-2-ethylhexyl Peroxydicarbonate in OMS | 1.0% DHDCHP in IPA | 63.4 | 34.6 |
| 75.5% Di-sec-butyl Peroxydicarbonate in OMS | none | 28.6 | 6.9 |
| 75% Di-sec-butyl Peroxydicarbonate in OMS | 1.0% DHDCHP in DMM | 30.2 | 11.2 |
| 75.5% Di-sec-butyl Peroxydicarbonate in OMS | 1.0% DHDCHP in EG | 35.6 | 8.8 |

DHDCHP = 1,1'-dihydroxy-dicyclohexyl peroxide
IPA = isoprpoyl alcohol
DMM = dimethyl malonate
EG = ethylene glycol

TABLE III

Purity vs. Time at 15° C. for Peroxydicarbonates Stabilized with α-Hydroxyalkyl Peroxides

| Peroxydicarbonate | Wt. % Pure Additive Used | % Purity After Storage | | | |
|---|---|---|---|---|---|
| | | 1 week | 2 weeks | 3 weeks | 4 weeks |
| 97.7% Di-2-ethylhexyl Peroxydicarbonate (pure) | none | 34.6 | 20.6 | 14.6 | 12.2 |
| 97.7% Di-2-ehylhexyl Peroxydicarbonate (pure) | 3.2% HMBP | 90.9 | 72.5 | 52.2 | 37.2 |
| 97.7% Di-2-ethylhexyl Peroxydicarbonate (pure) | 3.0% HMAP | 92.5 | 76.7 | 54.4 | 37.6 |
| 74.8% Di-2-ethylhexyl Peroxydicarbonate in OMS | none | 29.4 | 17.8 | 11.7 | 7.0 |
| 74.8% Di-2-ethylhexyl Peroxydicarbonate in OMS | 3.0% HMBP | 71.4 | 59.8 | 48.8 | 39.2 |
| 74.8% Di-2-ethylhexyl Peroxydicarbonate in OMS | 3.0% HMAP | 71.8 | 60.4 | 47.9 | 38.1 |
| 76.2% Di-sec-butyl Peroxydicarbonate in OMS | none | 17.1 | 3.7 | 3.8 | — |
| 76.2% Di-sec-butyl Peroxydicarbonate in OMS | 3.0% HMBP | 34.7 | 23.1 | 24.0 | — |
| 76.2% Di-sec-butyl Peroxydicarbonate in OMS | 3.0% HMAP | 34.6 | 12.6 | 7.8 | — |

HMBP = hydroxymethyl-t-butyl peroxide
HMAP = hydroxymethyl-t-amyl peroixde

We claim:

1. A composition comprising:
   a. an organic peroxide component selected from the group consisting of peroxydicarbonate compounds and mixtures thereof; and
   b. a sufficient amount of a stabilizer to retard the rate of decomposition of the organic peroxide component, wherein said stabilizer is selected from the group consisting of α-hydroxyalkyl peroxides of formulas I and II:

$$\begin{array}{cc} R^1 & OH \\ | & | \\ R^2-C-OO-C-R^4 \\ | & | \\ R^3 & R^5 \end{array} \quad (I)$$

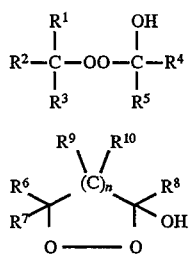

(II)

and mixtures thereof, wherein $R^1$ is hydrogen, hydroxy, alkyl containing 1 to 22 carbon atoms, phenyl, or phenyl substituted with one or more of alkyl containing 1–22 carbon atoms, halogen, and hydroxy;

$R^2$ and $R^3$ are each independently hydrogen, alkyl containing 1 to 22 carbon atoms, phenyl, or phenyl substituted with one or more of alkyl containing 1–22 carbon atoms, halogen, and hydroxy; or together $R^2$ and $R^3$ and the carbon atom to which they are attached may form a cycloalkyl ring containing from 4 to 10 carbon atoms;

$R^4$ and $R^5$ are each independently hydrogen, alkyl containing 1 to 22 carbon atoms, phenyl, or phenyl substituted with one or more of alkyl containing 1–22 carbon atoms, halogen, and hydroxy; or together $R^4$ and $R^5$ and the carbon atom to which they are attached may form a cycloalkyl ring containing from 4 to 10 carbon atoms;

in formula II, n is 1–10;

$R^6$ is hydrogen, alkyl containing 1 to 22 carbon atoms, hydroxy, phenyl, or phenyl substituted with one or more of alkyl containing 1–22 carbon atoms, halogen, and hydroxy;

$R^7$ and $R^8$ are each independently hydrogen, alkyl containing 1 to 22 carbon atoms, phenyl, or phenyl substituted with one or more of alkyl containing 1–22 carbon atoms, halogen, and hydroxy;

$R^9$ and $R^{10}$ are each independently hydrogen, alkyl containing 1 to 22 carbon atoms, phenyl, or phenyl substituted with one or more of alkyl containing 1–22 carbon atoms, halogen, and hydroxy.

2. A composition according to claim 1 comprising a compound of formula (I).

3. A composition according to claim 1 comprising a compound of formula (II).

4. A composition according to claim 1 comprising at least one compound selected from the group consisting of hydroxymethyl-tert-butyl peroxide, hydroxymethyl-tert-amyl peroxide, 1,1'-dihydroxy-dicyclohexyl peroxide, 3,5-dimethyl-3,5-dihydroxy-1,2-dioxacyclopentane, and 1,1'-dihydroxy dibenzyl peroxide.

5. A composition according to claim 1 wherein said stabilizer comprises 0.1 to 5.0% by weight of said peroxydicarbonate component.

6. A composition according to claim 1 wherein said organic peroxide component comprises at least one compound of the formula (III)

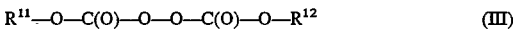

wherein $R^{11}$ and $R^{12}$ are independently aliphatic, cycloaliphatic or aromatic groups containing 1 to 22 carbon atoms.

7. A composition according to claim 6 wherein $R^{11}$ and $R^{12}$ are independently selected from the group consisting of phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxybutyl, 2-carbamyloxyethyl, 2-chloroethyl, 2-nitrobutyl and 2-nitro-2-methylpropyl.

8. A composition according to claim 1 wherein said peroxydicarbonate compounds are selected from the group consisting of di-2-ethylhexyl peroxydicarbonate, di-sec-butyl peroxydicarbonate, diethyl peroxydicarbonate, di-n-butyl peroxydicarbonate, isopropyl-sec-butyl peroxydicarbonate, di-4-tert-butylcyclohexyl peroxydicarbonate, di-n-propyl peroxydicarbonate, diisopropyl peroxydicarbonate, and mixtures thereof.

9. The method of inhibiting the rate of decomposition of a peroxydicarbonate compound comprising adding to said peroxydicarbonate a stabilizer in an amount thereof effective to inhibit said decomposition, wherein said stabilizer is selected from the group consisting of compounds of formulas I and II:

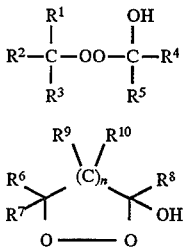

and mixtures thereof, wherein $R^1$ is hydrogen, hydroxy, alkyl containing 1 to 22 carbon atoms, phenyl, or phenyl substituted with one or more of alkyl containing 1–22 carbon atoms, halogen, and hydroxy;

$R^2$ and $R^3$ are each independently hydrogen, alkyl containing 1 to 22 carbon atoms, phenyl, or phenyl substituted with one or more of alkyl containing 1–22 carbon atoms, halogen, and hydroxy; or together $R^2$ and $R^3$ and the carbon atom to which they are attached may form a cycloalkyl ring containing from 4 to 10 carbon atoms;

$R^4$ and $R^5$ are each independently hydrogen, alkyl containing 1 to 22 carbon atoms, phenyl, or phenyl substituted with one or more of alkyl containing 1–22 carbon atoms, halogen, and hydroxy; or together $R^4$ and $R^5$ and the carbon atom to which they are attached may form a cycloalkyl ring containing from 4 to 10 carbon atoms;

in formula II, n is 1–10;

$R^6$ is hydrogen, alkyl containing 1 to 22 carbon atoms, hydroxy, phenyl, or phenyl substituted with one or more of alkyl containing 1–22 carbon atoms, halogen, and hydroxy;

$R^7$ and $R^8$ are each independently hydrogen, alkyl containing 1 to 22 carbon atoms, phenyl, or phenyl substituted with one or more of alkyl containing 1–22 carbon atoms, halogen, and hydroxy;

$R^9$ and $R^{10}$ are each independently hydrogen, alkyl containing 1 to 22 carbon atoms, phenyl, or phenyl substituted with one or more of alkyl containing 1–22 carbon atoms, halogen, and hydroxy.

10. A method according to claim 9 wherein the amount of said stabilizer is 0.1 to 5.0% by weight of said peroxydicarbonate.

11. A method according to claim 9 wherein said stabilizer is selected from the group consisting of hydroxymethyl tert-butyl peroxide, hydroxymethyl tert-amyl peroxide, 1,1'-dihydroxy dicyclohexyl peroxide, 1,1'-dihydroxy dibenzyl peroxide, and 3,5-dimethyl-3, 5-dihydroxy-1,2-dioxacyclopentane.

12. A method according to claim 9 wherein said peroxydicarbonate corresponds to formula (III)

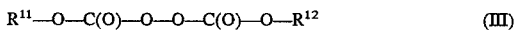

wherein $R^{11}$ and $R^{12}$ are independently aliphatic, cycloaliphatic or aromatic groups containing 1 to 22 carbon atoms.

13. A method according to claim 9 wherein $R^{11}$ and $R^{12}$ are independently selected from the group consisting of phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxybutyl, 2-carbamyloxyethyl, 2-chloroethyl, 2-nitrobutyl and 2-nitro-2-methylpropyl.

14. A method according to claim 9 wherein said peroxydicarbonate component is selected from the group consisting of di-2-ethylhexyl peroxydicarbonate, di-sec-butyl peroxydicarbonate, diethyl peroxydicarbonate, di-n-butyl peroxydicarbonate, isopropyl-sec-butyl peroxydicarbonate, di-4-tert-butylcyclohexyl peroxydicarbonate, di-n-propyl peroxydicarbonate, diisopropyl peroxydicarbonate, and mixtures thereof.

* * * * *

UNITED STATES PATENT AND TRADEMARK OFFICE
CERTIFICATE OF CORRECTION

PATENT NO. : 5,654,463

DATED : August 5, 1997

INVENTOR(S) : Charles Abma, et al

It is certified that error appears in the above-identified patent and that said Letters Patent is hereby corrected as shown below:

Column 9, line 14, "ehylhexyl" should read --ethylhexyl--.

Signed and Sealed this

Tenth Day of November 1998

Attest:

BRUCE LEHMAN

Attesting Officer

Commissioner of Patents and Trademarks